United States Patent [19]

Drabek et al.

[11] Patent Number: 4,584,296
[45] Date of Patent: Apr. 22, 1986

[54] PESTICIDAL COMPOSITIONS

[75] Inventors: Jozef Drabek, Oberwil; John Legge, Witterswil; Markus Bachmann, Riehen, all of Switzerland

[73] Assignee: Ciba-Geigy Corporation, Ardsley, N.Y.

[21] Appl. No.: 612,236

[22] Filed: May 21, 1984

[30] Foreign Application Priority Data

May 30, 1983 [CH] Switzerland ............... 2942/83
May 3, 1983 [CH] Switzerland ............... 297/83
May 3, 1983 [CH] Switzerland ............... 2944/83

[51] Int. Cl.$^4$ .................. A01N 57/10; A01N 43/40
[52] U.S. Cl. .................................. 514/147; 514/346
[58] Field of Search ............... 424/225, 324, 263; 514/147, 346

[56] References Cited

U.S. PATENT DOCUMENTS 4,436,737  3/1984  Boray ..................... 424/225

FOREIGN PATENT DOCUMENTS 57-77604  5/1982  Japan .

Primary Examiner—Leonard Schenkman
Assistant Examiner—Joseph A. Lipovsky
Attorney, Agent, or Firm—Edward McC. Roberts

[57] ABSTRACT

A pesticidal composition which contains, as active ingredient, a combination of the compound of the formula

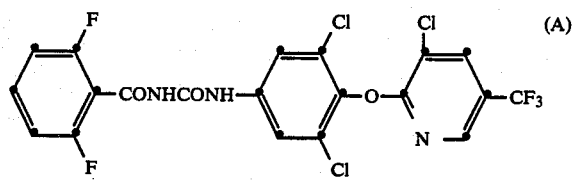

with a compound of the formula

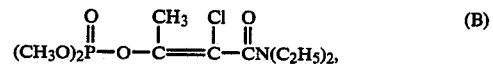

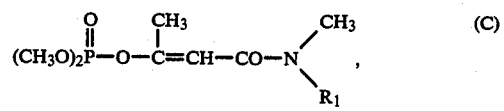

wherein $R_1$ is hydrogen or methyl,

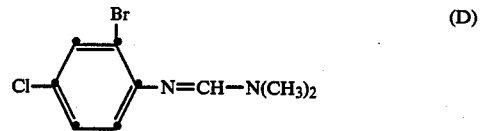

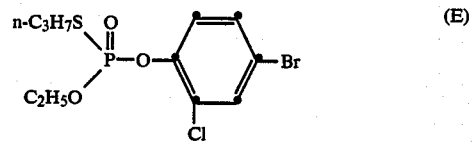

in a ratio of 1:20 to 10:1; as well as the use of the composition for controlling various pests on animals and plants, is described.

3 Claims, No Drawings

PESTICIDAL COMPOSITIONS

The present invention relates to pesticidal compositions which contain, as active ingredient, a combination of the benzoylurea of the formula

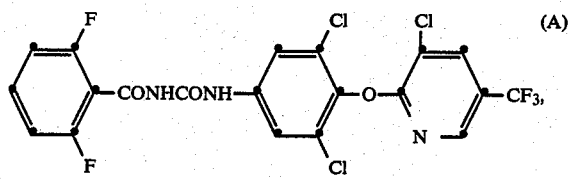

known from the British Patent Specification No. 1,589,259, with Phosphamidon of the formula

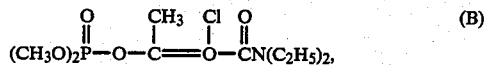

known from the U.S. Pat. No. 2,908,605, or with a phosphoric acid ester of the formula

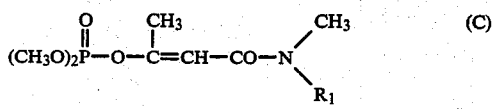

wherein $R_1$=hydrogen (Monocrotophos) or $R_1$=methyl (Dicrotophos), both known from the U.S. Pat. No. 2,802,855, or with Chlordimeform of the formula

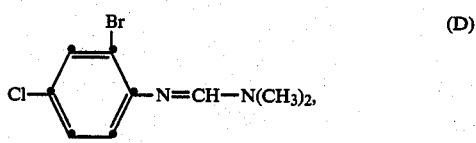

known from the U.S. Pat. No. 3,911,012, or with Profenofos of the formula

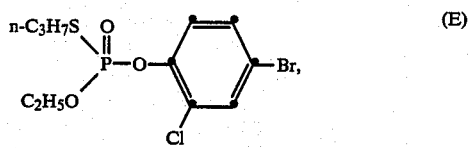

known from the German Offenlegungsschrift No. 2,249,462, in a ratio of 1:20 to 10:1, to the use thereof for controlling various pests on animals and plants, as well as to the use thereof in control processes in which the pesticides A, B, C, D or E to be mixed are used either successively with a short intervening time or simultaneously from different containers.

Mixtures of substances of various classes, for example of formamidines, ureas, carbamates, phosphoric acid esters or pyrethoids, have already been described as being synergistically effective preparations in the field of pest control. It has however been shown that the known combination preparations do not in every case satisfy to the desired extent the demands made of them in practice with respect in particular to effectiveness, toxicity and economy in application.

It has now been found that combinations of pesticide A with pesticide B, C, D or E in the ratio of 1:20 to 10:1, preferably 1:8 to 10:1, bring into effect a potentiating action against various pests on animals and plants, which surprisingly greatly exceeds the additive action of these combined active ingredients when used separately. The potentiating action of the pesticide A with pesticide B, C, D or E against various pests on animals and plants occurs in all control processes. There can thus be used processes in which the pesticide A and pesticides B, C, D and E, respectively, are applied premixed from one container or successively with a short intervening time or simultaneously from different containers to the locus of the pests.

The active-ingredient combinations of pesticide A with pesticide B, C, D or E are especially suitable for controlling all development stages of insects, for example of the orders: Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera; and also phytopathogenic and zooparasitic mites and ticks of the order Acarina.

The combinations of the pesticide A with pesticide B, C, D or E are suitable in particular however for controlling insects that damage plants, especially insects that damage plants by eating, in crops of ornamental plants and productive plants, particularly in cotton crops (for example against Spodoptera littoralis or Heliothis virescens), and in vegetable crops (for example against Leptinotarsa decemlineata or Myzus persicae).

The combinations of pesticide A with pesticide B, C, D or E have a very favourable potentiating action also against flies, for example *Musca domestica,* and against mosquito larvae. They are characterised also by a broad ovicidal and ovilarvicidal activity.

The combinations of pesticide A with pesticide B, C, D or E are used in preparations, together with auxiliaries customarily employed in formulation practice, and are thus processed in a known manner for example into the form of emulsion concentrates, suspension concentrates, directly sprayable or dilutable solutions, diluted emulsions, wettable powders, soluble powders, dusts or granulates, and also encapsulations in polymeric substances and the like. The application processes, such as spraying, atomising, dusting, scattering or pouring, are selected according to the intended use. It is to be ensured in this respect that the method of application and the nature and amount of the auxiliaries used for the preparation of the composition do not appreciably influence the biological behaviour of the active-ingredient combinations.

The preparations are produced in a known manner, for example by the intimate mixing and/or grinding of the active ingredient A with B, C, D or E, on their own or in combination with solvents, solid carriers and optionally surface-active substances (tensides). Suitable solvents are: aromatic hydrocarbons, preferably the fractions $C_8$ to $C_{12}$, that is, xylene mixtures up to substituted naphthalenes, aliphatic hydrocarbons, such as cyclohexane or paraffins, alcohols and glycols, as well as ethers and esters thereof, strongly polar solvents, such as dimethyl sulfoxide or dimethylformamide, and also water. The solid carriers used, for example for dusts and dispersible powders, are as a rule natural mineral fillers, such as calcite, talcum, kaolin, montmorillonite or attapulgite. To improve the physical properties, it is also possible to add highly dispersed silicic acid or highly dispersed absorbent polymers. Suitable granulated carriers are porous types, for example pumice, ground brick, sepiolite and bentonite; and suitable non-sorbent carriers are materials such as calcite or sand. There can also be used a great number of pre-granulated materials of inorganic or organic nature, such as dolomite or ground plant residues.

Depending on the nature of the active-ingredient-combination to be formulated, suitable surface-active substances are nonionic, cationic and/or anionic tensides having good emulsifying, dispersing and wetting properties.

Suitable cationic tensides are for example quaternary ammonium compounds, for example cetyltrimethylammonium bromide. Suitable anionic tensides are for example: soaps, salts of aliphatic monoesters of sulfuric acid, for example sodium lauryl sulfate, salts of sulfonated aromatic compounds, for example sodium dodecylbenzenesulfonate, sodium, calcium and ammonium lignin sulfonate, butylnaphthalenesulfonate and a mixture of the sodium salts of diisopropyl- and triisopropyl-naphthalenesulfonate. Suitable nonionic tensides are for example the condensation products of ethylene oxide with fatty alcohols, for example oleyl alcohol or cetyl alcohol, or with alkylphenols, for example octylphenol, nonylphenol and octylcresol. Other nonionic agents are the partial esters which are derived from long-chain fatty acids and hexite anhydrides, or condensation products of these partial esters with ethylene oxide, or phospholipides or lecethins.

The nonionic, anionic and cationic tensides customarily used in formulation practiced are described, inter alia, in the following publication:

"Mc Cutcheon's Detergents and Emulsifiers Annual", MC Publishing Corp., Ridgewood, N.J. (1979).

The preparations contain as a rule 0.1 99%, particularly 0.1 to 95%, of the active-ingredient combination A with B, C, D or E (ratio 1:20 to 10:1), 0 to 25% of a tenside and 1 to 99.9% of a solid or liquid additive.

The preparations can also contain other additives, such as stabilisers, antifoaming agents, viscosity regulators, binders and adhesives, as well as fertilisers, for obtaining special effects.

The active ingredients or active-ingredient-combinations of the pesticide A with pesticide B, C, D or E can be formulated for example as follows (values are given in percent by weight).

FORMULATION EXAMPLES FOR THE ACTIVE INGREDIENTS OR THE ACTIVE-INGREDIENT COMBINATIONS OF THE PESTICIDE A WITH THE PESTICIDE B, C, D OR E

| 1. Emulsion concentrates | (a) | (b) | (c) |
|---|---|---|---|
| active ingredient or active-ingredient combination | 25% | 40% | 5% |
| calcium dodecylbenzenesulfonate | 5% | 8% | — |
| castor oil-polyethylene glycol ether (36 mols of ethylene oxide) | 5% | — | 20% |
| tributylphenol-polyethylene glycol ether (30 mols of ethylene oxide) | — | 12% | 25% |
| cyclohexanone, | — | 15% | — |
| tetramethylurea | — | — | 35% |
| xylene mixture | 65% | 25% | — |
| butyl alcohol | — | — | 15%. |

Emulsions of any required concentration can be produced from concentrates of this type by dilution with water.

| 2. Solutions | (a) | (b) | (c) | (d) |
|---|---|---|---|---|
| active ingredient or active-ingredient combination | 80% | 10% | 5% | 95% |
| ethylene glycol-monomethyl ether | 20% | — | — | — |
| polyethylene glycol M.W. 400 | — | 70% | — | — |
| N—methyl-2-pyrrolidone | — | 20% | — | — |
| epoxidised coconut oil | — | — | 1% | 5% |
| ligroin (boiling limits 160–190° C.) | — | — | 94% | —. |

The solutions are suitable for application in the form of very small drops.

| 3. Granulates | (a) | (b) |
|---|---|---|
| active ingredient or active-ingredient combination | 5% | 10% |
| kaolin | 94% | — |
| highly dispersed silicic acid | 1% | — |
| attapulgite | — | 90%. |

The active ingredient or active-ingredient combination is dissolved in methylene chloride, the solution is sprayed onto the carrier, and the solvent is subsequently evaporated off in vacuo.

| 4. Dusts | (a) | (b) |
|---|---|---|
| active ingredient or active-ingredient combination | 2% | 5% |
| highly dispersed silicic acid | 1% | 5% |
| talcum | 97% | — |
| kaolin | — | 90%. |

Dusts ready for use are obtained by the intimate mixing together of the carriers with the active ingredient or with the active-ingredient combination A with B, C, D or E.

Test Example

Stomach-poison action/contact action against:
(a) Heliothis virescens $L_1$-larvae, normally sensitive (N),
(b) Heliothis virescens $L_1$-larvae, resistant (R).

Test plant

Cotton, 4-leaf stage (about 20 cm in height).

Test conditions

Storage of the cotton plants at 30° C.; 60% relative humidity.
Test at 28° C.; 60% relative humidity.

Test compounds

1. Benzoylurea A as 5% emulsion concentrate.
2. Phosphamidon B as 50% emulsion concentrate.
3. Chlordimeform D as 50% emulsion concentrate.
4. Profenofos E as 50% emulsion concentrate.

Test

Cotton plants are sprayed with the emulsions of the individual components and mixtures thereof, respectively, obtained from emulsion concentrates diluted with water to give the test concentration required, the amount applied in each case being equivalent to 100 liters/hectare. After the drying of the sprayed-on coatings, the plants are kept for 7 days at 30° C. with 60% relative humidity. The plants are subsequently placed into a 20 liter vessel and each is infested with 50 freshly emerged Heliothis virescens L$_1$-larvae [normally sensitive (N); resistant (R)].

An assessment is made after 4 days with respect to % mortality rate and damage caused by eating.

| 100 l/ha Test concentration in ppm | Compound A | | | | Compound B | | | | Mixture of compounds A + B | | | |
|---|---|---|---|---|---|---|---|---|---|---|---|---|
| | norm. sensitive *Heliothis virescens* L | | resistant *Heliothis virescens* L | | norm. sensitive *Heliothis Virescens* L | | resistant *Heliothis virescens* L | | norm. sensitive *Heliothis virescens* L | | resistant *Heliothis virescens* L | |
| | % mort. | eat.[1] | % mort. | eat.[1] | % mort. | eat.[1] | % mort. | eat.[1] | % mort. | eat.[1] | % mort. | eat.[1] |
| 3 | | | | | 40 | 1 | 35 | 1 | | | | |
| 25 | 60 | 2 | 45 | 1 | | | | | | | | |
| 3 + 25 | | | | | | | | | 90 | 3 | 80 | 3 |

| 100 l/ha Concentration in g of active ingredient or active-ingredient combination per hectare | Compound A norm. sensitive *Heliothis virescens* L | | Compound D Norm. sensitive *Heliothis Virescens* L | | Mixture of compounds A + D norm. sensitive *Heliothis virescens* L | |
|---|---|---|---|---|---|---|
| | % mort. | eat.[1] | % mort. | eat.[1] | % mort. | eat.[1] |
| 44 | 59 | 2 | | | | |
| 140 | | | 59 | 1 | | |
| 44 + 140 | | | | | 93 | 3 |

| 100 l/ha Test concentration in ppm | Compound A | | | | Compound E | | | | Mixture of compounds A + E | | | |
|---|---|---|---|---|---|---|---|---|---|---|---|---|
| | norm. sensitive *Heliothis virescens* L | | resistant *Heliothis virescens* L | | norm. sensitive *Heliothis Virescens* L | | resistant *Heliothis virescens* L | | norm. sensitive *Heliothis virescens* L | | resistant *Heliothis virescens* L | |
| | % mort. | eat.[1] | % mort. | eat.[1] | % mort. | eat.[1] | % mort. | eat.[1] | % mort. | eat.[1] | % mort. | eat.[1] |
| 3 | | | | | 25 | 1 | 0 | 1 | | | | |
| 25 | 60 | 2 | 45 | 1 | | | | | | | | |
| 3 + 25 | | | | | | | | | 85 | 3 | 75 | 3 |

Assessment of extent of eating damage (eat.)
[1] = as control plants
[2] = reduced damage compared with that on control plants
[3] = no eating/traces of eating

What is claimed is:
1. An insecticidal and acaricidal composition which contains, as active ingredient, a combination of the compound of the formula

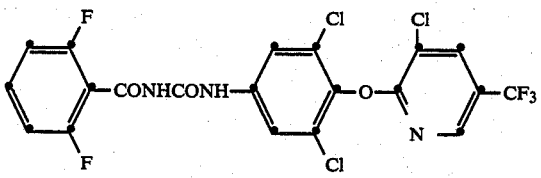

with a compound of the formula

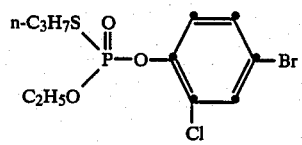

in a ratio of 3:25.

2. A process for controlling profenofos resistant strains of *heliothis virescens*, which method comprises applying thereto or to the locus thereof an effective amount of the active compound of the formula

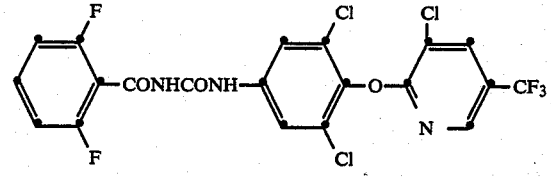

with a compound of the formula

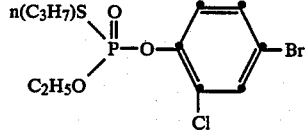

in a ratio of 3:25.

3. A process according to claim 2, which process comprises applying the two active compounds premixed from one container, or simultaneously from different containers.

* * * * *

UNITED STATES PATENT AND TRADEMARK OFFICE
CERTIFICATE OF CORRECTION

PATENT NO. : 4,584,296

DATED : April 22, 1986

INVENTOR(S) : Jozef Drabek, John Legge, Markus Bachmann

It is certified that error appears in the above-identified patent and that said Letters Patent is hereby corrected as shown below:

On the cover page, item 30, line 2 should read --
May 30, 1983 [CH] Switzerland............2943/83 --.

On the cover page, item 30, line 3 should read --
May 30, 1983 --.

Signed and Sealed this

Sixteenth Day of September 1986

[SEAL]

Attest:

DONALD J. QUIGG

Attesting Officer

Commissioner of Patents and Trademarks